United States Patent [19]

Messina et al.

[11] Patent Number: 4,615,346

[45] Date of Patent: Oct. 7, 1986

[54] PERMANENT WAVE TREATMENT TO HAIR AND MATERIAL USED THEREIN

[76] Inventors: Louis Messina, 8 Buckthorn La., Collegeville, Pa. 19426; Terry P. Hoffman, 3255 Sunset Ave., Eaglesville, Pa. 19403

[21] Appl. No.: 682,438

[22] Filed: Dec. 17, 1984

[51] Int. Cl.$^4$ ............................................... A45D 7/00
[52] U.S. Cl. .......................................... 132/7; 424/70
[58] Field of Search .................. 132/7, 39; 424/70–71

[56] References Cited

U.S. PATENT DOCUMENTS 2,906,273  9/1959  Beauregard ............................ 132/7

OTHER PUBLICATIONS

Hackh's Chemical Dictionary, Aug. 1975, author–Julius Grant, pp. 343 and 426.

*Primary Examiner*—Gregory E. McNeill
*Attorney, Agent, or Firm*—David J. Johns

[57] ABSTRACT

A test for the completeness of an application of neutralizer solution to hair during a permanent wave treatment is disclosed in which a small quantity of an acid-base indicator added to the neutralizer solution produces a visible change in the color of the end wraps.

10 Claims, No Drawings

PERMANENT WAVE TREATMENT TO HAIR AND MATERIAL USED THEREIN

BACKGROUND OF THE INVENTION

This invention relates to a method of determining the completeness of a permanent wave procedure performed on hair. More specifically, it relates to the use of a tracer chemical in one of the crucial steps of a permanent wave treatment to mark those curls which have been properly treated, thus avoiding the expensive and embarrassing need to repeat the entire procedure.

The present procedure of creating a so-called "permanent wave" in hair is a time-consuming multi-step process. The process involves wetting the hair, dividing the hair into sections, rolling each section of hair sandwiched between two end wraps onto perm rods, treating each rolled section of hair with permanent wave solution, allowing the solution time to alter the structure of the hair, rinsing the hair, blotting the hair dry, applying a neutralizer solution to each rolled section of hair which reestablishes structure to the hair in the rolled orientation, removing the perm rods, and a final rinsing or washing of the hair before it is cut, blown dry, or set.

Despite the fact that permanent wave treatments have been well known and have enjoyed considerable success for many years, there is presently no straightforward manner of determining, during the procedure, whether each and every rolled section of hair has been properly treated with the requisite solutions. Failure to apply a required solution to even one of the rolled sections requires the entire process to be repeated at a later time. The varying degrees of experience of hair salon personnel and the frequency of interruptions and diversions in hair salons often makes it difficult to assure that the solutions are applied in a systematic and uninterrupted manner. Accordingly, over 20% of all permanent wave treatments require a return visit and a retreatment to the inconvenience of customers and to the expense of the salon. Packaged in-home permanent wave products are similarly handicapped and, being typically applied by nonprofessionals, may experience an even greater percentage of required reapplications.

An object of the present invention is to provide a means of tracing the application of permanent wave treatment chemicals which is readily incorporated into standard methods for performing these treatments and which provide a straightforward and reliable method of determining which rolled sections of hair have or have not received treatment.

A further object of the present invention is to provide a means of tracing the application of permanent wave treatment chemicals which is inexpensive and convenient to use.

An additional object of the present invention is to provide a tracing element which readily mixes with existing permanent wave treatment chemicals, yet is non-toxic, will readily rinse from the hair, and will not disturb or alarm the client during treatment.

SUMMARY OF THE INVENTION

In the present invention there is provided a test for tracing the application of permanent wave treatment neutralizer solution consisting of the addition of small amounts of a water-soluble acid-base indicator such as Methyl Orange to commercially available neutralizer solution. The resulting mixture effectuates a color change in the end wraps which the hair is rolled within on the perm rods, but does not alter the qualities of the neutralizer solution or in any way bind to or damage the hair.

By providing a visual indication of which rolled sections of hair have been treated with neutralizing solution, the present invention assures that this crucial step, which re-establishes the structure of the hair in the rolled orientation, is complete.

The present invention functions with most, if not all, commercially available end wraps and permanent wave treatment neutralizer solutions, and it is simple and inexpensive to use.

The solution used in the present invention readily rinses from the hair, has no harmful side-effects, and can be used without disturbing or inconveniencing the customer.

Additionally, the present invention eliminates the costly and embarrassing need for retreatment due to the incomplete application of permanent wave neutralizer solution.

DETAILED DESCRIPTION OF THE INVENTION

A test for completeness of application of a permanent wave treatment for hair is provided. The test consists of the addition of a small quantity of an acid-base indicator to commercially available neutralizer solution. The addition of the improved neutralizer solution to rolled hair causes a color change in standard end wraps, but does not bind to or damage the hair.

In a typical permanent wave treatment for hair, the stylist must perform a multi-step procedure. First the hair is wetted and divided into sections. The hair sections, or portions thereof, are then sandwiched between two end wraps (or "end papers"). The sandwiched hair is rolled onto perm rods and each separately rolled section of hair is treated with permanent wave solution. After the permanent wave solution has had time to alter the structure of the hair, the rolled hair is rinsed and blotted dry. Neutralizer solution is then applied to each rolled section of hair which reestablishes the structure of the hair in the rolled orientation. Finally, the perm rods and end wraps are removed and the hair is rinsed or lightly washed before a final cut, blow dry, or set.

The present invention involves the addition of a small quantity of acid-base indicator to the neutralizer solution. In the selection of the acid-base indicator to be used, it is important that the indicator maintains a visible color which will be distinguishable from hair color at the pH of neutralizer solution—approximately pH 4. Further, it is desirable that the indicator mixes readily with the neutralizer solution and does not require the addition of costly and/or potentially dangerous solvents, such as ethyl or methyl alcohols. A listing of acid-base indicators, their pH ranges and related colors, and the standard requirements for their preparation may be found in *CRC Handbook of Chemistry and Physics*, 63rd Ed. Boca Raton, CRC Press, 1982, pp. D-157-158.

The addition of the following acid-base indicators within the given quantity ranges to a standard four (4) ounce preparation of neutralizer solution has been found to provide satisfactory results:

Methyl Violet: approximately 0.0025 gram (within a possible range of 0.00025 gram to 0.0050 gram, and ideally between 0.00050 gram and 0.0040 gram);

Congo Red: approximately 0.1 gram (within a possible range of 0.01 gram to 0.20 gram, and ideally between 0.05 gram and 0.15 gram);

Methyl Orange: approximately 0.01 gram (within a possible range of 0.005 gram to 0.5 gram, and ideally between 0.0075 gram and 0.40 gram).

It is preferable to use no more acid-base indicator than is necessary to effectuate a noticeable change in the color of the end wrap which can be contrasted with the color of the customer's hair. Accordingly, lighter colored hair may require less indicator in the neutralizer solution, and darker colored hair may require more indicator. The addition of too much acid-base indicator may result in a slight colored residue left in the hair. This can be removed by repeated rinsings, usually with no damage to the permanent wave treatment.

The use of Methyl Violet or Congo Red with certain hair colors, however, can cause a noticeable change in the color of the hair during the application process which may disturb the customer. Additionally, Methyl Violet, which is black at pH 4, does not provide a clear contrast when applied to dark hair. Methyl Violet also may stain the stylist's hands. Therefore, the preferred acid-base indicator for application to all hair colors is Methyl Orange.

Although standard solutions of acid-base indicator can be prepared before being added to the neutralizer solution, it has been found that the acid-base indicator can be added directly to standard neutralizer solution and dispersed by shaking. In all other respects the normal procedure for permanent wave treatments should be followed. The appearance of color on the end wraps of each rolled segment of hair during the neutralizer treatment assures the stylist that that segment has been treated.

The use of an acid-base indicator (particularly Methyl Orange) has provided satisfactory results as a tracer chemical when used with the neutralizer solutions and end wraps of all leading permanent wave treatments, including: "Feel So Lively" produced by Zotos International, Inc.; "Apple Pectin" produced by La Maur, Inc.; "Creative Curl" produced by Redken Laboratories, Inc.; "Kind to Color" produced by Clairol, Inc.; "Kind to Hair" produced by Clairol, Inc.; "A Nucleo A Perm" produced by La Maur, Inc.; "Rayette" produced by Faberge; "Sensory Perm" produced by Revlon, Inc.; and "Comforette" produced by Wella Corp.

While a particular embodiment of the present invention has been disclosed herein, it is not intended to limit the invention to such a disclosure, and changes and modifications may be incorporated and embodied within the scope of the following claims.

What I claim is:

1. An improved acid solution for use in permanent wave treatments of hair, wherein hair is sectioned and each section of hair is rolled between end wraps, a permanent wave solution is applied to said hair sections, and a neutralization step is later performed, the improvement which comprises providing an acid solution and an acid-base indicator combined in a single fluid for use in said neutralization step, said acid-base indicator producing a color change in said end wraps wherever applied to said hair sections and thereby confirming the completeness of said neutralization step when all of said end wraps show said color change.

2. A combination for testing for the completeness of application of neutralizer solution to hair during a permanent wave treatment comprising:
    a neutralizer solution, combined with an acid-base indicator which produces a visible color in said neutralizer solution; and
    an end wrap which will absorb said neutralizer solution and display the color of said acid-base indicator.

3. The combination in accordance with claim 2 wherein said neutralizer solution is an acidic preparation.

4. The combination in accordance with claim 3 wherein said acid-base indicator is Methyl Orange.

5. The combination according to claim 4 wherein the concentration of said Methyl Orange is between 0.00125 gram and 0.125 gram per ounce of said neutralizer solution.

6. The combination in accordance with claim 3 wherein said acid-base indicator is Methyl Violet.

7. The combination according to claim 6 wherein the concentration of said Methyl Violet is between 0.0000625 gram and 0.00125 gram per ounce of said neutralizer solution.

8. The combination in accordance with claim 3 wherein said acid-base indicator is Congo Red.

9. The combination according to claim 8 wherein the concentration of said Congo Red is between 0.0025 gram and 0.05 gram per ounce of said neutralizer solution.

10. A method of providing a permanent wave treatment to hair including the steps of
    wetting the hair,
    dividing the hair into sections,
    rolling said sections of hair between absorbent end wraps onto perm rods,
    applying permanent wave solution to each of said rolled sections of hair,
    allowing said permanent wave solution time to alter the structure of said hair,
    rinsing said rolled sections of hair,
    blotting said rolled sections of hair dry,
    applying to said rolled sections of hair neutralizer solution combined with an acid-base indicator which produces a visible color in said end wraps upon absorption of said neutralizer solution,
    visually inspecting said end wraps of each said rolled section of hair to observe color change resulting from absorption of said neutralizer solution by said end wraps,
    unrolling said sections of hair and removing said perm rods and said end wraps, and
    rinsing or washing said hair.

* * * * *